(12) United States Patent
Tomabechi et al.

(10) Patent No.: US 9,724,282 B2
(45) Date of Patent: Aug. 8, 2017

(54) STOMATOLOGICAL COMPOSITION

(71) Applicant: Nippon Zettoc Co., LTD., Tokyo (JP)

(72) Inventors: Yasuyuki Tomabechi, Tokyo (JP); Manami Sato, Tokyo (JP); Misao Yasumuro, Tokyo (JP)

(73) Assignee: Nippon Zettoc Co., Ltd., Tokyo (JP)

( * ) Notice: Subject to any disclaimer, the term of this patent is extended or adjusted under 35 U.S.C. 154(b) by 171 days.

(21) Appl. No.: 14/345,877

(22) PCT Filed: Sep. 28, 2012

(86) PCT No.: PCT/JP2012/075075
§ 371 (c)(1),
(2) Date: Mar. 19, 2014

(87) PCT Pub. No.: WO2013/047745
PCT Pub. Date: Apr. 4, 2013

(65) Prior Publication Data
US 2014/0234230 A1      Aug. 21, 2014

(30) Foreign Application Priority Data

Sep. 30, 2011   (JP) ................. 2011-217960

(51) Int. Cl.
| | |
|---|---|
| *A61K 8/64* | (2006.01) |
| *A61K 8/365* | (2006.01) |
| *A61K 8/66* | (2006.01) |
| *A61Q 11/00* | (2006.01) |
| *A61K 39/395* | (2006.01) |
| *A61K 8/98* | (2006.01) |
| *A61K 38/46* | (2006.01) |
| *A61K 38/48* | (2006.01) |
| *A61K 38/39* | (2006.01) |
| *A61K 8/65* | (2006.01) |
| *A61K 39/00* | (2006.01) |

(52) U.S. Cl.
CPC .............. *A61K 8/365* (2013.01); *A61K 8/64* (2013.01); *A61K 8/65* (2013.01); *A61K 8/66* (2013.01); *A61K 8/982* (2013.01); *A61K 38/39* (2013.01); *A61K 38/465* (2013.01); *A61K 38/48* (2013.01); *A61K 39/39591* (2013.01); *A61Q 11/00* (2013.01); *A61K 2039/542* (2013.01); *C07K 2317/11* (2013.01); *C07K 2317/23* (2013.01)

(58) Field of Classification Search
None
See application file for complete search history.

(56) References Cited

U.S. PATENT DOCUMENTS

| 4,986,981 A | 1/1991 | Glace et al. |
|---|---|---|
| 5,281,524 A | 1/1994 | Horikoshi et al. |
| 5,439,680 A | 8/1995 | Horikoshi et al. |
| 2007/0231277 A1 | 10/2007 | Sharma et al. |
| 2009/0274660 A1* | 11/2009 | Girsh .................. A61K 9/0095 424/93.3 |

FOREIGN PATENT DOCUMENTS

| CN | 1613344 A | 5/2005 |
|---|---|---|
| JP | 1503142 A | 10/1989 |
| JP | 01313438 A | 12/1989 |
| JP | 2641228 B2 | 8/1997 |
| JP | 2001181163 A | 7/2001 |
| JP | 2009532374 A | 9/2009 |
| JP | 2011084500 A | 4/2011 |
| WO | 8800043 A1 | 1/1988 |

OTHER PUBLICATIONS

Bizhanov, G.; Jonauskiene, L.; Hau, J. "A novel method, based on lithium sulfate precipitation for purification of chicken egg yolk immunoglobulin Y, applied to immunospecific antibodies against Sendai virus." Scandinavian Journal of Laboratory Animal Science, 2004, 31(3), pp. 121-130.*
Thunberg, T. "The Occurrence of Citric Acid in the Shell Substance of Eggs of Chickens, Ducks, and Geese" Acta Physiologica Scandinavica, Jan. 1949, 17(1), pp. 83-85, DOI: 10.1111/j.1748-1716.1949.tb00554.x.*
ICC The Common Ion Effect, Acid-Base Equilibria and Solubility Equilibria, Chapter 16, 22 pages (<faculty.icc.edu/bcook/chem132NT/acid_base_eq.pdf>, archived online, Sep. 6, 2004).*
Japanese Patent Office, Office Action Issued in Japanese Patent Application No. 2011-217960, Jun. 2, 2015, 14 pages.

(Continued)

*Primary Examiner* — Chris R Tate
*Assistant Examiner* — Aaron J Kosar
(74) *Attorney, Agent, or Firm* — McCoy Russell LLP

(57) ABSTRACT

A stomatological composition is provided. The stomatological composition is capable of stably compounding an antibody obtained from a hen egg yolk, and preventing diseases in an oral cavity such as odontonecrosis and periodontal disease from occurring, or improving such diseases in the oral cavity. The stomatological composition includes at least one selected from the group consisting of lipase, protease and the antibody obtained from the hen egg yolk, citric acid and a metal salt of citric acid. A total amount of the lipase, the protease and the antibody obtained from the hen egg yolk is in the range of 0.001 to 10 wt %. When an amount of the citric acid is defined as "A" [wt %] and an amount of the metal salt of citric acid is defined as "B" [wt %], the following relation is satisfied: $0.005 \leq A/B \leq 1$. Further, the stomatological composition of the present invention includes a polyglyceryl fatty acid ester or an amino acid-based ampholytic surfactant as a surfactant. Further, the stomatological composition of the present invention includes a collagen.

12 Claims, No Drawings

(56) References Cited

OTHER PUBLICATIONS

Colombia Industrial Property Office, Office Action Issued in Colombian Patent Application No. 14-39939-5, Jul. 2, 2015, 11 pages.
International Bureau of WIPO, Translation of International Preliminary Report on Patentability in Application No. PCT/JP2012/075075, Apr. 10, 2014, WIPO, 14 pages.
ISA European Patent Office, Extended European Search Report in Application No. PCT/JP2012/075075, Jul. 28, 2014, WIPO, 3 pages.
ISA Japanese Patent Office, International Search Report of PCT/JP2012/075075, Dec. 18, 2012, 4 pages.

* cited by examiner

STOMATOLOGICAL COMPOSITION

TECHNICAL FIELD

The present application relates to a stomatological composition.

RELATED ART

As one of causes of odontonecrosis, there is adhesion of dental plaque. It has been pointed out in the past that removal of the plaque and prevention of the adhesion (namely, the prevention of the adhesion of the dental plaque) are important in dental health. Plaque is made by allowing Streptococcus mutans (S. mutans) to adhere to a tooth surface firmly through insoluble glucan having viscosity. Such glucan is synthesized by membrane-bound glucosyltransferase, which is an enzyme produced from Streptococcus mutans, with use of sucrose as a substance Further, such adhesion of the dental plaque causes periodontal disease, which is a kind of inflammation, such as gingivitis, developed in periodontal tissue, periodontal infection, and pyorrhea alveolaris.

In order to prevent or improve a disease in an oral cavity, such as the odontonecrosis or the periodontal disease, a stomatological composition has been developed, which contains an antibody obtained from a hen egg yolk, an enzyme, and the like (for example, Patent Document 1 and Patent Document 2).

However, it is impossible to contain the antibody obtained from the hen egg yolk and the enzyme stably in an existing stomatological composition, so that it is difficult to sufficiently prevent plaque from adhering to teeth in a sustained manner. Therefore, prevention or improvement of the odontonecrosis and the periodontal disease has not been sufficiently achieved in the existing stomatological composition.

The Patent Document 1 is JP-B 2641228 which is an example of related art. The Patent Document 2 is JP-A 2001-181163 which is also an example of related art.

SUMMARY OF THE INVENTION

It is an object of the present invention to provide an stomatological composition that is capable of containing an antibody obtained from a hen egg yolk and an enzyme stably, thereby enabling a disease in an oral cavity such as odontonecrosis or periodontal disease to be prevented or improved.

Such an object is achieved by the present inventions (1) to (8) described below.

(1) A stomatological composition, comprising: at least one selected from the group consisting of lipase, protease and an antibody obtained from a hen egg yolk; citric acid; and a metal salt of citric acid.

(2) In one example of the stomatological composition in the above-mentioned item (1), a total amount of the lipase, the protease and the antibody obtained from the hen egg yolk is in the range of 0.001 to 10 wt %.

(3) As another example, in the stomatological composition in the above-mentioned item (1) or (2), when an amount of the citric acid is defined as "A" [wt %] and an amount of the metal salt of citric acid is defined as "B" [wt %], the following relation is satisfied: $0.005 \le A/B \le 1$.

(4) As another example, in the stomatological composition in any one of the above-mentioned items (1) to (3), when an amount of the citric acid is defined as "A" [wt %] and a total amount of the lipase, the protease and the antibody obtained from the hen egg yolk is defined as "C" [wt %], the following relation is satisfied: $0.0005 \le A/C \le 10000$.

(5) As a further example, in the stomatological composition in any one of the above-mentioned items (1) to (4), when an amount of the metal salt of citric acid is defined as "B" [wt %] and a total amount of the lipase, the protease and the antibody obtained from the hen egg yolk is defined as "C" [wt %], the following relation is satisfied: $0.005 \le B/C \le 10000$.

(6) As a further example, in the stomatological composition in any one of the above-mentioned items (1) to (5), the stomatological composition further comprises a polyglyceryl fatty acid ester or an amino acid-based ampholytic surfactant as a surfactant.

(7) As yet another example, in the stomatological composition in any one of the above-mentioned items (1) to (6), the stomatological composition further comprises a collagen.

(8) As still another example, in the stomatological composition in any one of the above-mentioned items (1) to (7), a salt concentration in the stomatological composition is in the range of 0.1 to 20%.

According to the stomatological composition of the present invention, it is possible to contain the antibody obtained from the hen egg yolk and the enzyme stably, thereby enabling the disease in the oral cavity such as the odontonecrosis or the periodontal disease to be prevented or improved.

MODE FOR CARRYING OUT THE INVENTION

Hereinbelow, description will be made on a stomatological composition according to the present invention in detail with reference to example embodiments.

In this regard, it is to be noted that the stomatological composition in this specification includes: a tooth agent such as a toothpaste agent, a tooth powder agent, a liquid-like tooth agent, and a liquid tooth agent; a lozenge; a tablet; a cream agent; an ointment agent; an adhesive skin patch; a mouth rinse agent; a chewing gum; and the like.

The stomatological composition of the present invention is used as a purpose of effects of suppressing plaque from being formed and preventing a disease in an oral cavity from being developed. It is characterized that the stomatological composition of the present invention contains at least one selected from the group consisting of lipase, protease and an antibody obtained from a hen egg yolk, citric acid, and a metal salt of citric acid.

Meanwhile, in order to prevent or improve a disease in an oral cavity such as odontonecrosis or periodontal disease, a stomatological composition has been developed, which contains an antibody obtained from a hen egg yolk. However, it is impossible to contain the antibody obtained from the hen egg yolk and an enzyme stably in an existing stomatological composition. Therefore, it is difficult to sufficiently prevent or improve the odontonecrosis and the periodontal disease in the existing stomatological composition.

In view of such problems, the present inventors have studied hard and developed a stomatological composition which contains citric acid and a metal salt of citric acid with the antibody obtained from the hen egg yolk and the enzyme as described later. By doing so, the present inventors have found that it is possible to contain the antibody obtained from the hen egg yolk and the enzyme as described later into the stomatological composition stably. As a result, the present inventors have found that it is possible for such a stomatological composition to exhibit excellent effects of preventing and improving the disease in the oral cavity.

Hereinafter, description will be made on each component in detail.

[Antibody Obtained from Hen Egg Yolk]

The antibody obtained from the hen egg yolk is an antibody obtained from a hen's egg in which an enzyme (antigen) produced from offending bacteria of the disease in the oral cavity is immunized. The antibody obtained from the hen egg yolk has a function of inactivating the enzyme produced from the offending bacteria of the disease in the oral cavity.

As described above, it has been impossible to contain such an antibody obtained from the hen egg yolk stably in the existing stomatological composition, thereby lowering the above function over time. Consequently, it has been impossible to exhibit a sufficient effect of preventing the disease in the oral cavity. In the present invention, the stomatological composition contains the antibody obtained from the hen egg yolk with components as described later. By doing so, it is possible to contain the antibody obtained from the hen egg yolk stably, so that it is possible to exhibit the function of the antibody obtained from the hen egg yolk stably. As a result, it is possible to exhibit the effects of preventing and improving the disease in the oral cavity.

Examples of the antibody obtained from the hen egg yolk include one obtained from a hen's egg in which an antigen produced from bacteria in the oral cavity such as *Streptococcus mutans*, *Porphyromonas gingivalis* and the like is immunized.

In particular, in the case where the antibody obtained from the hen egg yolk in which an enzyme produced from *Streptococcus mutans* is immunized is used, the following effects are obtained.

Generally, odontonecrosis of the disease in the oral cavity is caused by *Streptococcus mutans* of the bacteria in the oral cavity.

*Streptococcus mutans* produces membrane-bound glucosyltransferase in the oral cavity. The produced membrane-bound glucosyltransferase synthesizes insoluble glucan having viscosity with use of sucrose as a substance.

*Streptococcus mutans* adheres to a teeth surface firmly through the synthesized insoluble glucan to form plaque. This plaque makes odontonecrosis generate. Further, a periodontal disease such as gingival inflammation, periodontal infection and the like is developed by the existence of the plaque in the oral cavity for a long period of time.

When the stomatological composition contains the antibody obtained from the hen egg yolk with the enzyme produced from *Streptococcus mutans*, it is possible to efficiently prevent the plaque from adding to the teeth surface, thereby exhibiting the excellent effects of preventing the odontonecrosis and the periodontal disease. In other words, the antibody obtained from the hen egg yolk inactivates the enzyme produced from *Streptococcus mutans*. By doing so, it is possible to suppress a bio film (a layer of plaque) from being formed on the teeth surface due to the addition of the plaque thereto, so that it is possible to reliably prevent the odontonecrosis and the periodontal disease from occurring.

Among enzymes produced from *Streptococcus mutans*, the enzyme acting to the antibody obtained from the hen egg yolk is preferably membrane-bound glucosyltransferase which is an adhesion factor of *Streptococcus mutans* to the teeth. This makes it possible to prevent *Streptococcus mutans* from adhering to the teeth surface, thereby preventing the plaque from being adhered to the teeth surface more effectively. As a result, it is possible to reliably prevent the odontonecrosis and the periodontal disease from occurring more effectively.

The antibody obtained from the hen egg yolk acting to the membrane-bound glucosyltransferase can be obtained as an immune globulin prepared from an egg which is produced by hen and in which the membrane-bound glucosyltransferase is immunized.

As the immune globulin obtained as described above, the antibody not only acts to the adhesion factor of *Streptococcus mutans* to the teeth, but also suppresses the membrane-bound glucosyltransferase from being produced. As a result, it is possible to prevent the glucan from being synthesized and further effectively suppress the plaque from being formed.

The combination use of such an antibody obtained from the hen egg yolk and components as described later makes it possible to contain the antibody obtained from the hen egg yolk into the stomatological composition stably as well as suppress action of *Streptococcus mutans* more effectively. As a result, it is possible to prevent the disease in the oral cavity such as the odontonecrosis and the periodontal disease from occurring more effectively.

In the case where an antibody obtained from the hen egg yolk in which an enzyme produced from *Porphyromonas gingivalis* is immunized is used, the following effects are obtained.

*Porphyromonas gingivalis* dislikes an enzyme and exists in plaque. This *Porphyromonas gingivalis* produces protease named gingipains to grow proliferously. This protease breaks down gingival tissues, thereby progressing the inflammation of gum. Thus, the disease in the oral cavity progresses.

When the stomatological composition contains the antibody obtained from the hen egg yolk with the enzyme (gingipains) produced from *Porphyromonas gingivalis*, it is possible to inactivate the enzyme produced from *Porphyromonas gingivalis*. By doing so, it is possible to suppress the inflammation of gum from progressing, so that it is possible to prevent or improve the disease in the oral cavity more reliably.

[Lipase]

Lipase is a generic term for an enzyme catalyzing a hydrolysis of a fat and one of three major digestive enzymes together with amylase and protease. The lipase is a hydrolysis enzyme to break down a cell wall, a fat and a sugar. The lipase is an enzyme having a function of preventing activities of bacteria in the oral cavity by breaking down the cell wall of the bacteria in the oral cavity as well as the sugar to be used for the bacteria in the oral cavity.

It has been difficult for conventional stomatological compositions to contain lipase stably. However, it is possible for the present invention to contain lipase in the stomatological composition stably by the combination use of citric acid and the metal salt of citric acid, and the lipase.

Examples of the lipase include: one derived from an organ of a pig; one derived from a microbe; and the like. Specifically, examples of the lipase include one derived from genus *Pseudomonas* and one derived from genus *Bacillus*.

[Protease]

Protease is a generic term for an enzyme hydrolyzing a peptide (generally, includes residue structures lower than 100 and has relatively small molecular weight), in which amino acids are bonded with each other by a peptide bond in a chain manner, and a peptide bond of a protein (generally, includes the residue structures of 100 or more and has relatively large molecular weight).

A large amount of proteins is contained in the plaque. The protease has a function of decomposing and removing such proteins. The protease contained in the stomatological composition makes it possible to efficiently remove the plaque.

It has been difficult for the conventional stomatological compositions to contain protease stably. However, it is possible for the present invention to contain protease in the stomatological composition stably by the combination use of citric acid and the metal salt of citric acid, and the protease.

Examples of the protease include: subtilisin (produced by Novozymes), Alcalase (produced by Novozymes), Esperase (produced by Novozymes), Savinase (produced by Novozymes), Nagarse (produced by Nagase ChemteX Corporation), and API-21 (produced by SHOWA DENKO K.K.), which are produced by bacteria of genus *Bacillus*; Prozyme (produced by Amano Enzyme Inc.) produced by filamentous fungi of genus *Aspergillus*; serratio peptidase produced by bacteria of genus *Serratia*; and the like. Further, examples of the protease include papain and bromelain which are derived from fruit. Further, a culture solution of a protease production strain which is isolated from soil and the like may be also used as the protease.

A total amount of the antibody obtained from the hen egg yolk, the lipase and the protease as described above is preferably in the range of 0.001 to 10 wt %, and more preferably in the range of 0.05 to 5 wt %. This makes it possible to reliably suppress the action of the bacteria in the oral cavity. In contrast, if the total amount is smaller than the lower limit value noted above, it becomes difficult for an antibody having a sufficient amount to remain in the oral cavity. Consequently, there is a case that it becomes difficult to sufficiently suppress the action of the bacteria in the oral cavity. On the other hand, if the total amount exceeds the upper limit value noted above, there is a case that enough effects matching the amount may not be obtained.

[Citric Acid and Metal Salt of Citric Acid]

The stomatological composition of the present invention contains the citric acid and the metal salt of citric acid.

The citric acid and the metal salt of citric acid are components contributing to contain the antibody obtained from the hen egg yolk, the lipase and the protease into the stomatological composition stably. By containing such citric acid and a metal salt of citric acid, it is possible to stably exhibit the function of each of the antibody obtained from the hen egg yolk, the lipase and the protease. As a result, it is possible to prevent or improve the disease in the oral cavity such as the odontonecrosis and the periodontal disease. This is because of the following reasons.

The antibody obtained from the hen egg yolk includes a large amount of amino acids and constitutes a three-dimensional structure made with electrostatic force due to electric charges of the amino acids. However, the three-dimensional structure is fragile and is affected by moisture, a temperature, pH and a salt concentration. Therefore, if the citric acid and the metal salt of citric acid are contained in the stomatological composition, it is considered that it is possible to adjust suitable pH and suitable salt concentration with respect to the antibody obtained from the hen egg yolk and the like, thereby enabling further stable three-dimensional structure to be formed.

Examples of the metal salt of citric acid include: sodium citrate; potassium citrate; calcium citrate; magnesium citrate; copper citrate; and the like.

An amount of the citric acid in the stomatological composition is preferably in the range of 0.005 to 10 wt %, and more preferably in the range of 0.01 to 5 wt %. This makes it possible to contain the antibody obtained from the hen egg yolk, the lipase and the protease into the stomatological composition stably.

An amount of the metal salt of citric acid in the stomatological composition is preferably in the range of 0.05 to 10 wt %, more preferably in the range of 0.1 to 5 wt %, and even more preferably in the range of 0.2 to 1 wt %. This makes it possible to stably contain the antibody obtained from the hen egg yolk, the lipase and the protease into the stomatological composition more efficiently.

When the amount of the citric acid in the stomatological composition is defined as "A" [wt %] and the amount of the metal salt of citric acid in the stomatological composition is defined as "B" [wt %], the following relation is satisfied: preferably $0.005 \leq A/B \leq 1$, and more preferably $0.01 \leq A/B \leq 0.5$. By satisfying such a relation, it is possible to stably contain the antibody obtained from the hen egg yolk, the lipase and the protease into the stomatological composition more efficiently. In particular, it is possible to improve the stabilization of the antibody obtained from the hen egg yolk conspicuously.

Further, when the amount of the citric acid is defined as "A" [wt %] and the total amount of the lipase, the protease and the antibody obtained from the hen egg yolk in the stomatological composition is defined as "C" [wt %], the following relation is satisfied: preferably $0.0005 \leq A/C \leq 10000$, and more preferably $0.002 \leq A/C \leq 2000$. By satisfying such a relation, it is possible to stably contain the antibody obtained from the hen egg yolk, the lipase and the protease into the stomatological composition more efficiently. In particular, it is possible to improve the stabilization of the antibody obtained from the hen egg yolk conspicuously.

Further, when the amount of the metal salt of citric acid is defined as "B" [wt %] and the total amount of the lipase, the protease and the antibody obtained from the hen egg yolk is defined as "C" [wt %], the following relation is satisfied: preferably $0.005 \leq B/C \leq 10000$, and more preferably $0.01 \leq B/C \leq 2000$. By satisfying such a relation, it is possible to stably contain the antibody obtained from the hen egg yolk, the lipase and the protease into the stomatological composition more efficiently. In particular, it is possible to improve the stabilization of the antibody obtained from the hen egg yolk conspicuously.

Other Components

The stomatological composition of the present invention may contain any components as described below other than the above components.

[Collagen]

The stomatological composition of the present invention may contain a collagen.

The collagen is a component contributing to contain the antibody obtained from the hen egg yolk, the lipase and the protease into the stomatological composition stably. The combination use of the citric acid and the metal salt of citric acid and the collagen makes it possible to contain the antibody obtained from the hen egg yolk, the lipase and the protease into the stomatological composition stably. Therefore, it is possible to exhibit the function of each of the antibody obtained from the hen egg yolk, the lipase and the protease further stably. As a result, it is possible to prevent or improve the disease in the oral cavity such as the odontonecrosis and the periodontal disease more efficiently.

Examples of the collagen include: a fibrous collagen such as I to III type collagens, a V type collagen and the like; a non-fibrillar collagen such as a IV type collagen, VI to VIII type collagens and the like; a hydrolyzed collagen (collagen peptide) obtained by hydrolyzing these collagens with an acid or an enzyme; a soluble collagen (atelocollagen); gelatin; and the like.

Among them, in the case where the hydrolyzed collagen is used, it is possible to contain the antibody obtained from the hen egg yolk, the lipase and the protease into the stomatological composition stably, thereby enabling the function of each of the antibody obtained from the hen egg yolk, the lipase and the protease to exhibit more effectively. As a result, it is possible to reliably prevent or improve the disease in the oral cavity.

In this regard, the hydrolyzed collagen is a high pure protein obtained by hydrolyzing a large amount of collagens included in skins of fish, bovine and pigs with an acid, a basic and the like to obtain a low-molecular compound thereof and absorb it inside the body with ease. Such a collagen may be derived from fish (skin, scale and the like) or a mammal such as the bovine and the pigs (skin and the like), and further other living organism (hen and the like). Examples of the fish is not limited particularly, but include chum salmon, trout, pollock, mackerel, horse mackerel, sea bream, tilapia nilotica, bass, herring, carp, gibel, and the like. In this regard, it is to be noted that the obtained hydrolyzed collagen may be used as a solution, a concentrated solution in which the solution is concentrated if needed, and a solid which is obtained by evaporating all the liquid in the solution.

Further, the gelatin is a component having the range of several tens of thousands of a molecular weight to several hundreds of thousands of the molecular weight, which is obtained by decomposing the collagen and purifying it.

An amount of the collagen in the stomatological composition is preferably in the range of 0.01 to 10 wt %, and more preferably in the range of 0.1 to 5 wt %. This makes it possible to stably contain the antibody obtained from the hen egg yolk, the lipase and the protease into the stomatological composition more effectively, thereby enabling the function of each of the antibody obtained from the hen egg yolk, the lipase and the protease to further exhibit efficiently. As a result, it is possible to prevent or improve the disease in the oral cavity more reliably.

Further, when the total amount of the antibody obtained from the hen egg yolk, the lipase and the protease is defined as "C" [wt %] and the amount of the collagen in the stomatological composition is defined as "D" [wt %], the following relation is satisfied: preferably $0.001 \leq D/C \leq 10000$, and more preferably $0.02 \leq D/C \leq 100$. This makes it possible to stably contain the antibody obtained from the hen egg yolk, the lipase and the protease into the stomatological composition more efficiently.

Further, the stomatological composition of the present invention may contain various kinds of components other than the above components, depending on a form thereof. For example, in the case where the stomatological composition of the present invention is applied to a toothpaste agent, the stomatological composition may contain an abrading agent, a wetting agent, a binder, a forming agent (surfactant), a sweetening agent, an antiseptic agent, a flavor ingredient, a medicated component other than these agents and the like.

Examples of the abrading agent include: a silica-based abrading agent such as a silica gel, silica having sedimentation property, silica having pyrogenic property, hydrated silicate, anhydrous silicic acid, aluminosilicate, and zirconosilicate; calcium hydrogen phosphate for brushing of teeth such as dicalcium phosphate dehydrate, and dicalcium phosphate non-hydrate; calcium pyrophosphate; trimagnesium phosphate; tricalcium phosphate; aluminum hydroxide; alumina; light calcium carbonate; heavy calcium carbonate; magnesium carbonate; zirconium silicate; a synthetic resin-based abrading agent; and the like. These materials may be used singly or in combination of two or more of them.

An amount of the abrading agent in the stomatological composition is not limited particularly, but is preferably in the range of 3 to 60 wt %, and more preferably in the range of 10 to 45 wt %.

Examples of the wetting agent include: a polyol such as glycerin, concentrated glycerin, diglycerin, sorbitol, maltitol, dipropylene glycol, propylene glycol, 1,3-butylene glycol, and xylitol; and the like. These materials may be used singly or in combination of two or more of them.

An amount of the wetting agent in the stomatological composition is not limited particularly, but is preferably in the range of 1 to 60 wt %, and more preferably in the range of 5 to 50 wt %.

Examples of the binder include: an alginate such as carrageenan (t, λ,), algin acid, sodium alginate, propylene glycol alginate, calcium-containing sodium alginate, potassium alginate, calcium alginate, and ammonium alginate; derivatives thereof; xanthane gum; guar gum; gelatin; an agar, carboxymethylcellulose sodium; hydroxyethyl cellulose; sodium polyacrylate; and the like. These materials may be used singly or in combination of two or more of them.

An amount of the binder in the stomatological composition is not limited particularly, but is preferably in the range of 0.1 to 5.0 wt %, and more preferably in the range of 0.5 to 3.0 wt %.

Examples of the forming agent (surfactant) include: sodium lauryl sulfate; sodium lauroampho acetate; sodium alkylsulfo succinate; coconut oil fatty acid monoglycerin sodium slufonate; α-olefin sodium slufonate; an N-acylamino acid salt such as N-acyl glutamate; an amino acid-based ampholytic surfactant such as 2-alkyl-N-carboxymethyl-N-hydroxyethyl imidazolinium betaine and sodium undecylhydroxyethyl imidazolinium betaine; a maltitol fatty acid ester; a sucrose fatty acid ester; a polyglyceryl fatty acid ester; fatty acid diethanolamide, polyoxyethylene sorbitan monostearate; a polyoxyethylene hydrogenated castor oil; a polyoxyethylene fatty acid ester; and the like. These materials may be used singly or in combination of two or more of them.

Among them, in the case where the polyglyceryl fatty acid ester and/or the amino acid-based ampholytic surfactant is used, it is possible to contain the antibody obtained from the hen egg yolk, the lipase and the protease into the stomatological composition stably, thereby enabling the function of each of the antibody obtained from the hen egg yolk, the lipase and the protease to exhibit stably. As a result, it is possible to prevent or suppress the disease in the oral cavity from occurring more reliably.

Further, it is preferred that an ester of polyclycerol and a fatty acid having a carbon number in the range of 12 to 16 is used as the polyglyceryl fatty acid ester. This makes it possible to contain the antibody obtained from the hen egg yolk, the lipase and the protease into the stomatological composition further stably, thereby enabling the function of each of the antibody obtained from the hen egg yolk, the lipase and the protease to exhibit stably. As a result, it is possible to prevent or suppress the disease in the oral cavity from occurring further efficiently.

An amount of the forming agent (surfactant) in the stomatological composition is not limited particularly, but is preferably in the range of 0.1 to 10.0 wt %, and more preferably in the range of 0.5 to 5.0 wt %.

Further, when the total amount of the antibody obtained from the hen egg yolk, the lipase and the protease is defined as "C" [wt %] and the amount of the forming agent in the stomatological composition is defined as "E" [wt %], the following relation is satisfied: preferably $0.01 \le E/C \le 10000$, and more preferably $0.1 \le E/C \le 100$. This makes it possible to stably contain the antibody obtained from the hen egg yolk, the lipase and the protease into the stomatological composition more efficiently.

Examples of the sweetening agent include saccharin sodium, aspartame, trehalose, stevioside, stevia extracts, paramethoxy cinnamic aldehyde, neohesperidin dihydrochalcone, perillartin, and the like. These materials may be used singly or in combination of two or more of them.

An amount of the sweetening agent in the stomatological composition is not limited particularly, but is preferably in the range of 0.005 to 5.0 wt %, and more preferably in the range of 0.01 to 3.0 wt %.

Examples of the antiseptic agent include: a paraben such as methylparaben, ethylparaben, propylparab en, and butylparaben; sodium benzoate; phenoxyethanol; alkyldiaminoehhylglycine hydrochloride; and the like. These materials may be used singly or in combination of two or more of them.

An amount of the antiseptic agent in the stomatological composition is dependent from a kind thereof, but is preferably in the range of 0.005 to 5.0 wt %, and more preferably in the range of 0.01 to 3.0 wt %.

Examples of the flavor ingredient include 1-menthol, anethole, menthone, cineol, limonene, carvone, methyl salicylate, ethyl butyrate, eugenol, thymol, cinnamic aldehyde, trans-2-hexenal, and the like. These materials may be used singly or in combination of two or more of them. These materials may be contained in the stomatological composition by themselves. Alternatively, an essential oil containing these materials and the like may be contained in the stomatological composition. Further, in addition to the above flavor ingredient, the stomatological composition may contain an aliphatic alcohol, an ester thereof, a terpene hydrocarbon, phenol ether, aldehyde, ketone, another flavor ingredient such as lactone, and an essential oil within a scope not to prevent the effects of the present invention.

An amount of the flavor ingredient in the stomatological composition is not limited particularly, but is preferably in the range of 0.02 to 2 wt %, and more preferably in the range of 0.05 to 1.5 wt %.

Examples of the medicated component include monofluorophosphate, sodium fluoride, potassium fluoride, sodium monofluorophosphate, polyethylene glycol, polyvinylpyrrolidone, zeolite, hinokitiol, a chlorhexidine salt, cetylpyridinium chloride, benzalkonium chloride, benzethonium chloride, dequalinium chloride, triclosan, isopropyl methyl phenol, bisabolol, ascorbic acid and/or derivatives thereof, tocopherol acetate, $\epsilon$-aminocaproic acid, tranexamic acid, aluminum hydroxyl allantoin, aluminum lactate, dihydrocholesterol, glycyrrhetinic acid, glycyrrhizinate, a copper chlorophyllin salt, guaiazulene sulfonate, dextranase, pyridoxine hydrochloride, zeolite, and the like. These materials may be used singly or in combination of two or more of them.

The stomatological composition may contain a pigment such as brilliant blue FCF; a colorant such as titanic oxide; an antioxidant such as dibutylhydroxyltoluene; a tea extract; a tea tar; a flavoring substance such as glutamic sodium; and the like other than the above components.

A salt concentration of the stomatological composition as described above is preferably in the range of 0.1 to 20%, and more preferably in the range of 0.5 to 15%. This makes it possible to stably contain the antibody obtained from the hen egg yolk, the lipase and the protease into the stomatological composition further effectively.

Here, the term "salt concentration" means a total concentration of salts contained in the stomatological composition.

The stomatological composition of the present invention obtained by combining the above components is produced in the usual manner. The producing method is not limited particularly. In particular, it is preferred that the antibody obtained from the hen egg yolk is added into the stomatological composition in a state of dissolving the antibody obtained from the hen egg yolk with the collagen to water. This makes it possible to contain the antibody obtained from the hen egg yolk into the stomatological composition stably. As a result, it is possible to exhibit the function of the antibody obtained from the hen egg yolk more reliably, so that it is possible to efficiently prevent or suppress the disease in the oral cavity from occurring.

The obtained stomatological composition such as a tooth agent can be used by filling it into an aluminum tube, a laminate tube, a glass deposition tube, a plastic tube, a plastic bottle, an aerosol container, and the like.

The stomatological composition of the present invention has been described. However, the present invention is not limited thereto. For example, the stomatological composition of the present invention may contain any component having an arbitrary function other than the components described above.

EXAMPLES

Next, description will be made on concrete examples of the invention.

Example 1

First, a toothpaste agent of the stomatological composition was produced by using the following components 1 to 11 (unit: wt %).

In this regard, an immune globulin was used as the antibody obtained from the hen egg yolk. Such an immune globulin was prepared from an egg which was produced by hen and in which the membrane-bound glucosyltransferase of *Streptococcus mutans* was immunized. The toothpaste agent was produced in the usual manner, except that the antibody obtained from the hen egg yolk was added to water with a hydrolysis collagen to dissolve them.

1. Antibody obtained from the hen egg yolk: 1.0
2. Citric acid: 0.08
3. Sodium citrate: 1.0
4. Hydrolysis collagen: 0.5
5. Polyglyceryl monolaurate: 0.2
6. Xylitol: 1.0
7. Concentrated glycerin: 20.0
8. Sorbitol: 40.0
9. Carboxymethylcellulose sodium: 2.7
10. Perfume material: 1.0
11. Distilled water: residue Examples 2 to 10

In each of the Examples 2 to 10, a toothpaste agent was produced in the same manner as the Example 1, except that an amount of each of the antibody obtained from the hen egg yolk, the citric acid and the metal salt of citric acid was changed as shown in Table 1.

Example 11

A toothpaste agent was produced in the same manner as the Example 1, except that the immune globulin as the antibody obtained from the hen egg yolk was changed to an immune globulin prepared from an egg which was produced by hen and in which the gingipains of *Porphyromonas gingivalis* was immunized, the hydrolysis collagen was changed gelatin, and 2-alykyl-N-carboxymethyl-N-hydroxyethyl imidazolinium betaine as a surfactant instead of polyglyceryl monolaurate was contained in an amount shown in Table 1.

Example 12

A toothpaste agent of the stomatological composition was produced by using the following components 1 to 13 (unit: wt %).

In this regard, an immune globulin was used as the antibody obtained from the hen egg yolk. Such an immune globulin was prepared from an egg which was produced by hen and in which the membrane-bound glucosyltransferase of *Streptococcus mutans* was immunized. The toothpaste agent was produced in the usual manner, except that the antibody obtained from the hen egg yolk was added to water with a hydrolysis collagen to dissolve them.
1. Antibody obtained from the hen egg yolk: 1.0
2. Citric acid: 0.08
3. Sodium citrate: 1.0
4. Hydrolysis collagen: 1.0
5. Polyglyceryl monolaurate: 2.0
6. Calcium hydrogen phosphate: 25.0
7. Silicic anhydride: 7.0
8. Xylitol: 1.0
9. Concentrated glycerin: 25.0
10. Carboxymethylcellulose sodium: 1.0
11. Polyethyelene glycol 400: 2.0
12. Perfume material: 1.0
13. Distilled water: residue

Example 13

A toothpaste agent of the stomatological composition was produced by using the following components 1 to 11 (unit: wt %).

In this regard, the toothpaste agent was produced in the usual manner, except that lipase was added to water with a hydrolysis collagen to dissolve them.
1. Lipase (derived genus *Pseudomonas*): 1.0
2. Citric acid: 0.08
3. Sodium citrate: 1.0
4. Hydrolysis collagen: 0.5
5. Polyglyceryl monolaurate: 0.2
6. Xylitol: 1.0
7. Concentrated glycerin: 20.0
8. Sorbitol: 40.0
9. Carboxymethylcellulose sodium: 2.7
10. Perfume material: 1.0
11. Distilled water: residue

Examples 14 to 22

In each of the Examples 14 to 22, a toothpaste agent was produced in the same manner as the Example 13, except that an amount of each of the lipase, the citric acid and the metal salt of citric acid was changed as shown in Table 2.

Example 23

A toothpaste agent was produced by using the following components 1 to 11 (unit: wt %).

In this regard, the toothpaste agent was produced in the usual manner, except that protease was added to water with a hydrolysis collagen to dissolve them.
1. Protease (papain): 1.0
2. Citric acid: 0.08
3. Sodium citrate: 1.0
4. Hydrolysis collagen: 0.5
5. Polyglyceryl monolaurate: 0.2
6. Xylitol: 1.0
7. Concentrated glycerin: 20.0
8. Sorbitol: 40.0
9. Carboxymethylcellulose sodium: 2.7
10. Perfume material: 1.0
11. Distilled water: residue

Examples 24 to 32

In each of the Examples 24 to 32, a toothpaste agent was produced in the same manner as the Example 23, except that an amount of each of the protease, the citric acid and the metal salt of citric acid was changed as shown in Table 2.

Comparative Example 1

A toothpaste agent was produced in the same manner as the Example 1, except that no citric acid was contained in the toothpaste agent.

Comparative Example 2

A toothpaste agent was produced in the same manner as the Example 1, except that no sodium citrate was contained in the toothpaste agent and the surfactant shown in Table 1 was used.

Comparative Example 3

A toothpaste agent was produced in the same manner as the Example 1, except that both the citric acid and the sodium citrate were not contained in the toothpaste agent and the surfactant shown in Table 1 was used.

Comparative Example 4

A toothpaste agent was produced in the same manner as the Example 13, except that no citric acid was contained in the toothpaste agent.

Comparative Example 5

A toothpaste agent was produced in the same manner as the Example 13, except that no sodium citrate was contained in the toothpaste agent and the surfactant shown in Table 2 was used.

Comparative Example 6

A toothpaste agent was produced in the same manner as the Example 13, except that both the citric acid and the sodium citrate were not contained in the toothpaste agent and the surfactant shown in Table 2 was used.

Comparative Example 7

A toothpaste agent was produced in the same manner as the Example 23, except that no citric acid was contained in the toothpaste agent.

Comparative Example 8

A toothpaste agent was produced in the same manner as the Example 23, except that no sodium citrate was contained in the toothpaste agent and the surfactant shown in Table 2 was used.

Comparative Example 9

A toothpaste agent was produced in the same manner as the Example 23, except that both the citric acid and the sodium citrate were not contained in the toothpaste agent and the surfactant shown in Table 2 was used.

In each of the Examples and the Comparative Examples, the kind and the amount of the antibody obtained from the hen egg yolk or the enzyme, the amount of each of the citric acid, the sodium citrate and the sodium chloride, the kind and the amount of each of the collagen and the surfactant, and the like were shown in Table 1 and Table 2. Further, in Tables, indicated were the antibody obtained from the hen egg yolk as the immune globulin prepared from the egg, which was produced by hen and in which the membrane-bound glucosyltransferase of *Streptococcus mutans* was immunized, as "X", the antibody obtained from the hen egg yolk as the immune globulin prepared from the egg, which was produced by hen and in which the gingipains of *Porphyromonas gingivalis* was immunized, as "Y", the lipase as "L", the protease as "P", the hydrolysis collagen as "a", the gelatin as "b", the polyglyceryl monolaurate as "A", the sodium lauroampho acetate as "B", and the 2-alkyl-N-carboxymethy-N-hydroxyethyl imidazolinium betaine as "C".

TABLE 1

| | Toothpaste agents | | | | | | | | | | | | | |
|---|---|---|---|---|---|---|---|---|---|---|---|---|---|---|
| | Antibodies obtained from hen egg yolk | | Citric acids | Metal salts of citric acid | Collagens | | Surfactants | | | | | | | Salt concentrations [%] | Evaluations of stable containing |
| | kinds | Amounts C[wt %] | Amounts A[wt %] | Amounts B[wt %] | kinds | Amounts D[wt %] | kinds | Amounts E[wt %] | A/B | A/C | B/C | D/C | E/C | | |
| Ex. 1 | X | 1 | 0.08 | 1 | a | 0.5 | A | 0.2 | 0.08 | 0.08 | 1 | 0.5 | 0.2 | 1 | A |
| Ex. 2 | X | 1 | 0.75 | 3 | a | 0.5 | A | 0.2 | 0.25 | 0.75 | 3 | 0.5 | 0.2 | 3 | B |
| Ex. 3 | X | 1 | 0.03 | 6 | a | 0.5 | A | 0.2 | 0.005 | 0.08 | 6 | 0.5 | 0.2 | 6 | C |
| Ex. 4 | X | 1 | 0.01 | 0.5 | a | 0.5 | A | 0.2 | 0.02 | 0.01 | 0.5 | 0.5 | 0.2 | 0.5 | A |
| Ex. 5 | X | 1 | 0.02 | 2 | a | 0.5 | A | 0.2 | 0.01 | 0.02 | 2 | 0.5 | 0.2 | 2 | B |
| Ex. 6 | X | 1 | 0.6 | 1 | a | 0.5 | A | 0.2 | 0.6 | 0.6 | 1 | 0.5 | 0.2 | 1 | B |
| Ex. 7 | X | 1 | 0.009 | 1 | a | 0.5 | A | 0.2 | 0.009 | 0.009 | 1 | 0.5 | 0.2 | 1 | C |
| Ex. 8 | X | 0.1 | 0.08 | 1 | a | 0.5 | A | 0.2 | 0.08 | 0.8 | 10 | 5 | 2 | 1 | A |
| Ex. 9 | X | 0.1 | 0.75 | 3 | a | 0.5 | A | 0.2 | 0.25 | 7.5 | 30 | 5 | 2 | 3 | B |
| Ex. 10 | X | 0.1 | 0.03 | 6 | a | 0.5 | A | 0.2 | 0.006 | 0.3 | 60 | 5 | 2 | 6 | C |
| Ex. 11 | Y | 1 | 0.08 | 1 | b | 0.5 | C | 0.2 | 0.08 | 0.08 | 1 | 0.5 | 0.2 | 1 | A |
| Ex. 12 | X | 1 | 0.08 | 1 | a | 1.0 | A | 2.0 | 0.08 | 0.08 | 1 | 1 | 2 | 1 | A |
| Com. Ex. 1 | X | 1 | — | 1 | a | 0.5 | A | 0.2 | — | — | 1 | 0.5 | 0.2 | 1 | D |
| Com. Ex. 2 | X | 1 | 0.08 | — | a | 0.5 | B | 0.2 | — | 0.08 | — | 0.5 | 0.2 | — | D |
| Com. Ex. 3 | X | 1 | — | — | a | 1.5 | B | 1.2 | — | — | — | 1.5 | 1.2 | — | D |

TABLE 2

| | Toothpaste agents | | | | | | | | | | | | | |
|---|---|---|---|---|---|---|---|---|---|---|---|---|---|---|
| | Enzymes | | Citric acids | Metal salts of citric acid | Collagens | | Surfactants | | | | | | | Salt concentrations [%] | Evaluations of stable containing |
| | kinds | Amounts C[wt %] | Amounts A[wt %] | Amounts B[wt %] | Kinds | Amounts D[wt %] | kinds | Amounts E[wt %] | A/B | A/C | B/C | D/C | E/C | | |
| Ex. 13 | L | 1 | 0.08 | 1 | a | 0.5 | A | 0.2 | 0.08 | 0.08 | 1 | 0.5 | 0.2 | 1 | A |
| Ex. 14 | L | 1 | 0.75 | 3 | a | 0.5 | A | 0.2 | 0.25 | 0.75 | 3 | 0.5 | 0.2 | 3 | B |
| Ex. 15 | L | 1 | 0.03 | 6 | a | 0.5 | A | 0.2 | 0.005 | 0.03 | 6 | 0.5 | 0.2 | 6 | C |
| Ex. 16 | L | 1 | 0.01 | 0.5 | a | 0.5 | A | 0.2 | 0.02 | 0.01 | 0.5 | 0.5 | 0.2 | 0.5 | A |
| Ex. 17 | L | 1 | 0.02 | 2 | a | 0.5 | A | 0.2 | 0.01 | 0.02 | 2 | 0.5 | 0.2 | 2 | B |
| Ex. 18 | L | 1 | 0.6 | 1 | a | 0.5 | A | 0.2 | 0.6 | 0.6 | 1 | 0.5 | 0.2 | 1 | B |
| Ex. 19 | L | 1 | 0.009 | 1 | a | 0.5 | A | 0.2 | 0.009 | 0.009 | 1 | 0.5 | 0.2 | 1 | C |
| Ex. 20 | L | 0.1 | 0.08 | 1 | a | 0.5 | A | 0.2 | 0.08 | 0.8 | 10 | 5 | 2 | 1 | A |
| Ex. 21 | L | 0.1 | 0.75 | 3 | a | 0.5 | A | 0.2 | 0.25 | 7.5 | 30 | 5 | 2 | 3 | B |
| Ex. 22 | L | 0.1 | 0.03 | 6 | a | 0.5 | A | 0.2 | 0.005 | 0.3 | 60 | 5 | 2 | 6 | C |

TABLE 2-continued

| | | | Toothpaste agents | | | | | | | | | | | | |
|---|---|---|---|---|---|---|---|---|---|---|---|---|---|---|---|
| | | Enzymes | Citric acids | Metal salts of citric acid | Collagens | | Surfactants | | | | | | | Salt concentrations [%] | Evaluations of stable containing |
| | kinds | Amounts C[wt %] | Amounts A[wt %] | Amounts B[wt %] | Kinds | Amounts D[wt %] | kinds | Amounts E[wt %] | A/B | A/C | B/C | D/C | E/C | | |
| Ex. 23 | P | 1 | 0.08 | 1 | a | 0.5 | A | 0.2 | 0.08 | 0.08 | 1 | 0.5 | 0.2 | 1 | A |
| Ex. 24 | P | 1 | 0.75 | 3 | a | 0.5 | A | 0.2 | 0.25 | 0.75 | 3 | 0.5 | 0.2 | 3 | B |
| Ex. 25 | P | 1 | 0.03 | 6 | a | 0.5 | A | 0.2 | 0.005 | 0.03 | 6 | 0.5 | 0.2 | 6 | C |
| Ex. 26 | P | 1 | 0.01 | 0.5 | a | 0.5 | A | 0.2 | 0.02 | 0.01 | 0.5 | 0.5 | 0.2 | 0.5 | A |
| Ex. 27 | P | 1 | 0.02 | 2 | a | 0.5 | A | 0.2 | 0.01 | 0.02 | 2 | 0.5 | 0.2 | 2 | B |
| Ex. 28 | P | 1 | 0.6 | 1 | a | 0.5 | A | 0.2 | 0.6 | 0.6 | 1 | 0.5 | 0.2 | 1 | B |
| Ex. 29 | P | 1 | 0.009 | 1 | a | 0.5 | A | 0.2 | 0.009 | 0.009 | 1 | 0.5 | 0.2 | 1 | C |
| Ex. 30 | P | 0.1 | 0.08 | 1 | a | 0.5 | A | 0.2 | 0.08 | 0.8 | 10 | 5 | 2 | 1 | A |
| Ex. 31 | P | 0.1 | 0.75 | 3 | a | 0.5 | A | 0.2 | 0.25 | 7.5 | 30 | 5 | 2 | 3 | B |
| Ex. 32 | P | 0.1 | 0.03 | 6 | a | 0.5 | A | 0.2 | 0.005 | 0.3 | 60 | 5 | 2 | 6 | C |
| Com. Ex. 4 | L | 1 | — | 1 | a | 0.5 | A | 0.2 | — | — | 1 | 0.5 | 0.2 | 1 | D |
| Com. Ex. 5 | L | 1 | 0.08 | — | a | 0.5 | B | 0.2 | — | 0.08 | — | 0.5 | 0.2 | — | D |
| Com. Ex. 6 | L | 1 | — | — | a | 1.5 | B | 1.2 | — | — | — | 1.5 | 1.2 | — | D |
| Com. Ex. 7 | P | 1 | — | 1 | a | 0.5 | A | 0.3 | — | — | 1 | 0.5 | 0.2 | 1 | D |
| Com. Ex. 8 | P | 1 | 0.08 | — | a | 0.5 | B | 0.2 | — | 0.08 | — | 0.5 | 0.2 | — | D |
| Com. Ex. 9 | P | 1 | — | — | a | 1.5 | B | 1.2 | — | — | — | 1.5 | 1.2 | — | D |

Evaluations

[Evaluation of Stable Containing of Antibody Obtained from the Hen Egg Yolk]

In the toothpaste agent obtained in each of the Examples 1 to 12 and the Comparative Examples 1 to 3, the toothpaste agent of 1 g just after the production thereof and the tooth agent of 1 g after it was stored at a temperature of 40° C. for 6 months were suspended in a phosphate buffered saline (PBS) of 9 mL to obtain a solution. The solution was incubated in a water bath of 37° C. for 15 minutes. Chloroform of 10 mL was added into the solution to obtain a mixture. The mixture was incubated in a water bath of 37° C. for 15 minutes. Thereafter, the mixture was subjected to a centrifugal separation for 20 minutes to obtain a water phase part. Thus, the water phase part was used as a sample solution. The sample solution was added into an ELISA plate, on which a solid phase antigen was adsorbed, at a ratio of 100 μL/well. The ELISA plate was left at 25° C. for 1 hour to carry out an antigen-antibody reaction. After the completion of the reaction, the ELISA plate was washed with PBS-T five times. Moreover, 100 μL of a peroxidase bonding anti-chicken IgG antibody as a secondary antibody was added to the ELISA plate to carry out the antigen-antibody reaction at 25° C. for 30 minutes. Thereafter, the ELISA plate was washed with the PBS-T six times. Next, 100 μL of a solution, in which phenylenediamine of 20 mg of a substrate and hydrogen peroxide of 10 μL were dissolved, was added into 50 mL of a 0.2 M disodium phosphate-0.1 M citric acid buffer solution (pH 5.0). Thus, a mixture was obtained. Thereafter, the mixture was reacted at 25° C. for 20 minutes. The reaction stoppage was performed by adding 100 μL of a 3N sulfuric acid solution into the mixture. After the completion of the reaction, an absorbance (OD490) of the obtained reaction solution was measured to obtain an antibody value. An amount of the antibody value obtained by using the toothpaste agent stored at 40° C. for 6 months with respect to an antibody value obtained by using the toothpaste agent just after the production was obtained. The amount was evaluated according to the following four criteria as a residual ratio of the antibody obtained from the hen egg yolk.

A: A residual ratio of the antibody obtained from the hen egg yolk is 80% or more.

B: A residual ratio of the antibody obtained from the hen egg yolk is 70% or more but lower than 80%.

C: A residual ratio of the antibody obtained from the hen egg yolk is 50% or more but lower than 70%.

D: A residual ratio of the antibody obtained from the hen egg yolk is lower than 50%.

[Evaluation of Stable Containing of Lipase]

In the toothpaste agent obtained in each of the Examples 13 to 22 and the Comparative Examples 4 to 6, the toothpaste agent of 5.0 g just after the production thereof and the toothpaste agent of 5.0 g after it was stored at a temperature of 40° C. for 6 months were suspended in a 0.1 M phosphate buffer solution (pH 7.0) of 10 mL to obtain a suspension liquid. Next, the suspension liquid was subjected to a centrifugal separation for 5 minutes to obtain a centrifugal supernatant. 2 mL of a 0.1 M phosphate buffer solution (pH 7.0) was added into 1 mL of the centrifugal supernatant to obtain a mixture A. The mixture A was heated for 5 minutes in a constant temperature reservoir of 37° C. Further, 3 mL of an olive oil emulsified liquid heated at 37° C. for 5 minutes in advance was added into the mixture A to obtain a mixture B. The mixture B was stirred at 37° C. for 30 minutes. Thereafter, 20 mL of a mixture of equal parts of acetone and ethanol was added into the mixture B to obtain a sample solution.

Aside from this, in the toothpaste agent obtained in each of the Examples 13 to 22 and the Comparative Examples 4 to 6, the toothpaste agent of 5.0 g just after the production thereof and the toothpaste agent of 5.0 g after it was stored at a temperature of 40° C. for 6 months were suspended in 10 mL of a 0.1 M phosphate buffer solution (pH 7.0) to obtain a suspension liquid. Next, the suspension liquid was subjected to a centrifugal separation for 5 minutes to obtain a centrifugal supernatant. 2 mL of a 0.1 M phosphate buffer solution (pH 7.0) of 2 mL was added into 1 mL of the centrifugal supernatant to obtain a mixture C. Furthermore, 20 mL of a mixture of equal parts of acetone and ethanol was added into the mixture C, and then it was mixed sufficiently. Thereafter, 3 mL of an olive oil emulsified liquid was added into the mixture C to obtain a mixture D. The mixture D was stirred at 37° C. for 30 minutes to obtain a control solution.

Three droplets of phenolphthalein were added into the sample solution and the control solution, respectively, to titrate with a 0.1 N sodium hydroxide solution. A lipase titer (unit/g) was calculated by the following formula. An amount of the lipase titer obtained by using the toothpaste agent stored at 40° C. for 6 months with respect to a lipase titer obtained by using the toothpaste agent just after the production was obtained. The amount was evaluated according to the following four criteria as a residual ratio of the lipase.

Lipase titer [unit/g]=[400×(a−b)]/3 where "a" represents a titer (mL) of the sample solution and "b" represents a titer (mL) of the control solution.

A: A residual ratio of the lipase is 80% or more.
B: A residual ratio of the lipase is 70% or more but lower than 80%.
C: A residual ratio of the lipase is 50% or more but lower than 70%.
D: A residual ratio of the lipase is lower than 50%.

[Evaluation of Stable Containing of Protease]

In the toothpaste agent obtained in each of the Examples 23 to 32 and the Comparative Examples 7 to 9, 20 mL of water was accurately added into the toothpaste agent of 0.25 g just after the production thereof and the toothpaste agent of 0.25 g after it was stored at a temperature of 40° C. for 6 months. They were mixed and suspended to obtain suspension liquids, respectively. Thereafter, the suspension liquid was subjected to a centrifugal separation for 5 minutes to obtain a centrifugal supernatant. 4 mL of a 0.1 mol/L phosphate buffer solution was added into 1 mL of the centrifugal supernatant to obtain a mixture E. The mixture E was heated for 5 minutes in a constant temperature reservoir of 30° C. Further, 4 mL of a 0.1 mol/L p-tosyl arginine methylester hydrochloride heated at 30° C. for 5 minutes in advance was added into the mixture E to obtain a mixture F. The mixture F was heated at 30° C. for 30 minutes, and then was filtered immediately (a membrane filter having a pore size of 0.45 μm). Then, 0.4 mL of a trichloroacetic acid solution (15→100) was added into 0.6 mL of the obtained filtrate to stop an enzyme reaction. Thus, a mixture G was obtained. Next, 0.2 mL of a potassium permanganate solution (2→100) was added into the mixture G to obtain a mixture H. The mixture H was stirred and left for 1 minute. The contents thereof were oxidized, and thereafter, 0.2 mL of a sodium acid sulfite solution (1→10) was added into the mixture H to obtain a mixture I. The mixture I was stirred and excess potassium permanganate was reduced. Next, 8 mL of a 0.4% chromotropic acid solution was added into the mixture I to obtain a mixture J. The mixture J was stirred well and heated in a boiling-water bath for 15 minutes accurately. Thus, the mixture J was colored. The mixture J was left at room temperature for 40 minutes. Thereafter, an absorbance in a wavelength of 580 nm of the mixture J was measured by using a blank solution of water. Similarly, a blank test was carried out, and a protease titer [unit/g] was obtained by the following formula. An amount of the protease titer obtained by using the toothpaste agent stored at 40° C. for 6 months with respect to a protease titer obtained by using the toothpaste agent just after the production was obtained. The amount was evaluated according to the following four criteria as a residual ratio of the protease.

Protease titer [unit/g]=(a−b)×188 where "a" represents an absorbance of the sample solution and "b" represents an absorbance of the sample solution for the blank test.

A: A residual ratio of the protease is 80% or more.
B: A residual ratio of the protease is 70% or more but lower than 80%.
C: A residual ratio of the protease is 50% or more but lower than 70%.
D: A residual ratio of the protease is lower than 50%.

The results evaluated as described above are shown in Table 1 and Table 2.

As shown in Table 1 and Table 2 clearly, the toothpaste agent obtained in each of the Examples could contain the lipase, the protease and the antibody obtained from the hen egg yolk stably.

In contrast, the toothpaste agent obtained in each of the Comparative Examples could obtain insufficient results.

INDUSTRIAL APPLICABILITY

The present invention provides with the stomatological composition comprising at least one selected from the group consisting of the lipase, the protease and the antibody obtained from the hen egg yolk, citric acid, and the metal salt of citric acid. According to the present invention, it is possible to provide with the stomatological composition that is capable of containing the antibody obtained from the hen egg yolk and the enzyme stably, and preventing or improving the disease in the oral cavity such as odontonecrosis or periodontal disease. Accordingly, the present invention has industrial applicability.

What is claimed is:

1. A stomatological composition comprising:
   (C) at least one selected from a group consisting of lipase, protease and an antibody obtained from a hen egg yolk;
   (A) citric acid; and
   (B) sodium citrate,
   wherein (A) and (B), by weight percent (wt %) of each in the composition, are present in the composition in a ratio of $0.01 \leq A/B \leq 0.5$, where (A) is present in the composition in a range of $0.005 \leq A \leq 0.08$ and (B) is present in the composition in a range of $0.2 \leq B \leq 1$ so that the composition can contain the lipase, the protease, and the antibody obtained from the hen egg yolk stably therein.

2. The stomatological composition as claimed in claim 1, wherein a total amount of the lipase, the protease and the antibody obtained from the hen egg yolk is in a range of 0.001 to 10 wt %.

3. The stomatological composition as claimed in claim 2, further comprising a polyglyceryl fatty acid ester or an amino acid-based ampholytic surfactant as a surfactant.

4. The stomatological composition as claimed in claim 1, wherein (A) and (C), by weight percent (wt %) of each in the composition, are present in the composition in a ratio of $0.0005 \leq A/C \leq 10000$.

5. The stomatological composition as claimed in claim 4, wherein (B) and (C), by weight percent (wt %) of each in the composition, are present in the composition in a ratio of $0.005 \leq B/C \leq 10000$.

6. The stomatological composition as claimed in claim 5, further comprising a polyglyceryl fatty acid ester or an amino acid-based ampholytic surfactant as a surfactant.

7. The stomatological composition as claimed in claim 6, further comprising a collagen.

8. The stomatological composition as claimed in claim 7, wherein a salt concentration in the stomatological composition is in a range of 0.1 to 20%.

9. The stomatological composition as claimed in claim 1, wherein (B) and (C), by weight percent (wt %) of each in the composition, are present in the composition in a ratio of $0.005 \leq B/C \leq 10000$.

10. The stomatological composition as claimed in claim 1, further comprising a collagen.

11. The stomatological composition as claimed in claim 1, further comprising a polyglyceryl fatty acid ester or an amino acid-based ampholytic surfactant as a surfactant.

12. The stomatological composition as claimed in claim 1, wherein a salt concentration in the stomatological composition is in a range of 0.1 to 20%.

* * * * *